Figure 1:
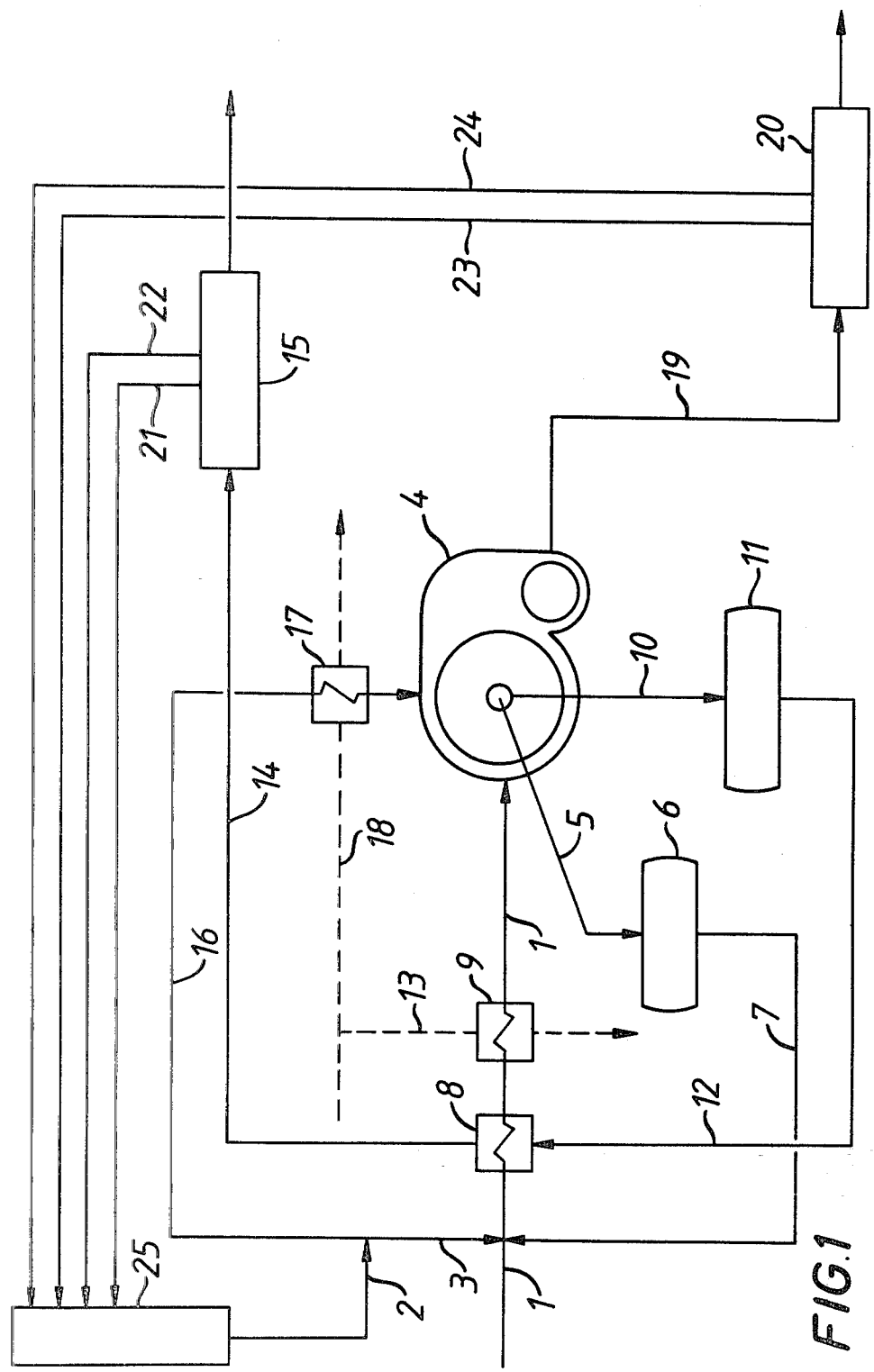

| United States Patent [19] | [11] 4,358,360 |
|---|---|
| Richter | [45] Nov. 9, 1982 |

[54] DEWAXING PROCESS

[75] Inventor: Ferdinand Richter, Hamburg, Fed. Rep. of Germany

[73] Assignee: British Petroleum Company Limited, London, England

[21] Appl. No.: 169,311

[22] Filed: Jul. 16, 1980

[30] Foreign Application Priority Data

Jul. 27, 1979 [DE] Fed. Rep. of Germany ....... 2930485
Jul. 27, 1979 [DE] Fed. Rep. of Germany ....... 2930486

[51] Int. Cl.$^3$ ......................... C10G 73/14; B01D 3/34
[52] U.S. Cl. ..................................... 208/33; 196/14.5; 203/29; 203/33; 203/37; 203/39; 203/96; 570/262
[58] Field of Search ................... 203/7, 33, 39, 29, 34, 203/37, 14, 92, 93, 38, 95-97; 196/14.5, 14.52; 208/33-35; 570/262

[56] References Cited

U.S. PATENT DOCUMENTS

| 2,589,212 | 3/1952 | Agapetus et al. | 203/37 |
| 3,448,016 | 6/1969 | Hoppe | 196/14.5 |
| 3,565,786 | 2/1971 | Brown et al. | 196/14.5 |
| 3,660,248 | 5/1972 | Tsao | 203/7 |
| 3,846,253 | 12/1974 | Obrecht | 203/33 |
| 3,998,706 | 12/1976 | Fruhwirt et al. | 203/7 |

OTHER PUBLICATIONS

Di-Me Solvent Dewaxing & Wax Deoiling Hydrocarbon Processing (Sep. 1978), p. 181.

Primary Examiner—Wilbur L. Bascomb, Jr.
Attorney, Agent, or Firm—Morgan, Finnegan, Pine, Foley and Lee

[57] ABSTRACT

Halogenated hydrocarbon and uncontaminated water is recovered from a stream of process water contaminated with halogenated hydrocarbon and hydrogen halide. The process water is neutralized and then distilled to obtain a first fraction containing halogenated hydrocarbon and water and a second fraction containing uncontaminated water. The first fraction is allowed to settle into layers of halogenated hydrocarbon and water which are then removed.

The contaminated stream may be obtained from a process for the solvent dewaxing of a petroleum fraction.

6 Claims, 4 Drawing Figures

DEWAXING PROCESS

This invention relates to a process for recovering halogenated hydrocarbons from process streams in which they are mingled with water and in particular to recovering such materials from a process for removing wax from hydrocarbon fractions by solvent dewaxing using halogenated hydrocarbons as the solvent.

It is necessary to remove high melting components from natural and synthetic hydrocarbon oils if the former solidify under temperature conditions at which the oils are to be used.

Many processes are known for this separation, known as dewaxing. In order to achieve low pour points in the case of the higher-boiling hydrocarbon fractions, solvent dewaxing is used preferentially. Usually the solvents used are mixtures whose components have differing solvent powers for the oil and the waxy components.

Mixtures of chlorinated hydrocarbons, especially of 1,2-dichlorethane and dichlormethane are especially advantageous. Such a process including solvent recovering is described, for example, in Erdöl and Kohle—Erdgas—Petrochemie, 17th year, No. 6, Pages 455–457, 1964.

As chlorinated hydrocarbons, however, are not completely stable chemically and thermally, in the course of time corrosion occurs in the plant as the result of hydrochloric acid which results from decomposition in the presence of water. As a result of this it is not only the process which is disturbed; harmful effects may also be observed on the quality of the oils and waxes recovered. Moreover the effluent from the plant contains not inconsiderable quantities of iron salts.

The presence of water in certain process streams is mainly caused by the fact that when recovering the solvent from the oily filtrate or wax collected in the dewaxing stage, steam is used for solvent stripping and also to produce a vacuum necessary for mild distillation by means of steam ejectors. Furthermore, small quantities of water are constantly brought into the plant with the feedstock.

The quantities of water introduced into the process, it is true, are to a large extent removed again in the solvent recovery, for example, by distillation according to the process described in DE-PS 917 865. However, on the whole this only prevents disorders caused by crystals of ice precipitated in the cold, for example, by obstructing the filter during the separation of the wax.

To avoid corrosion and the difficulties connected with it, it is known from DE-PS 918 651 that when recovering the solvent from the oily filtrate by distillation, evaporators connected in series at a temperature of not more than 100° C. can be employed. It has been found that the corrosion can certainly be diminished to some extent by this measure, but in the course of time some parts of the plant, especially those in which water separates out in the liquid phase, are so badly damaged that they have to be replaced.

Attempts have also been made to solve the corrosion problem by constantly injecting into the plant small quantities of ammonia (Winnacker-Küchler, Chemische Technologie, Vol. 3, Organische Technologie I, Page 306, 1959). But even with this measure, the defects referred to, especially in the solvent recovery, do not disappear. Furthermore, when ammonia is added, deposits of iron hydroxides or iron oxides form at many points, as a result of which serious upsets in the process may occur. At the very least a periodical cleaning of heat exchangers, condensers, pipes, tanks and other important parts of the plant is necessary.

It has now surprisingly been found that the disadvantages described do not occur if the plant is operated in the absence of ammonia and the hydrochloric acid present in a given process stream in the solvent recovery section of the dewaxing plant is neutralised with alkali hydroxides and/or alkali carbonates and/or alkali hydrogen carbonates, or removed from the same process stream with conventional ion exchangers. As a result of this not only are corrosion and deposits considerably reduced but further advantages in the form of a reduction in the iron content of the effluent from the plant and also improvements in certain properties of the dewaxed oil and wax are achieved.

Thus according to the present invention there is provided a process for the recovery of halogenated hydrocarbon and uncontaminated water from a stream of process water contaminated with halogenated hydrocarbon and hydrogen halide which process comprising the steps of neutralising the process water by treatment with an alkali metal hydroxide, carbonate or hydrogen carbonate, or an ion exchanger; distilling the treated stream to obtain a first fraction containing halogenated hydrocarbon and water and a second fraction containing uncontaminated water; allowing the first fraction to settle into layers of halogenated hydrocarbon and water; and removing the layer of halogenated hydrocarbon.

The contaminated process stream may be obtained from a process for the solvent dewaxing of a hydrocarbon fraction which comprises the steps of cooling the fraction in the presence of a halogenated hydrocarbon solvent; removing solidified wax and recovering solvent from the dewaxed fraction and the wax by recovery systems involving the use of steam wherein streams of process water containing halogenated hydrocarbon and hydrogen halide are formed. In this case, the recovered halogen hydrocarbon will preferably be recycled.

The halogenated hydrocarbon is preferably a chlorinated hydrocarbon and in this case the hydrogen halide will, of course, be hydrogen chloride.

Preferably the process stream containing halogenated hydrocarbon halide is neutralised by treatment with sodium hydroxide, most preferably with a 10% wt aqueous sodium hydroxide solution.

Preferably the treated stream is distilled in the presence of steam to obtain the first fraction containing halogenated hydrocarbon and water and the second fraction containing uncontaminated water.

Figure 2:
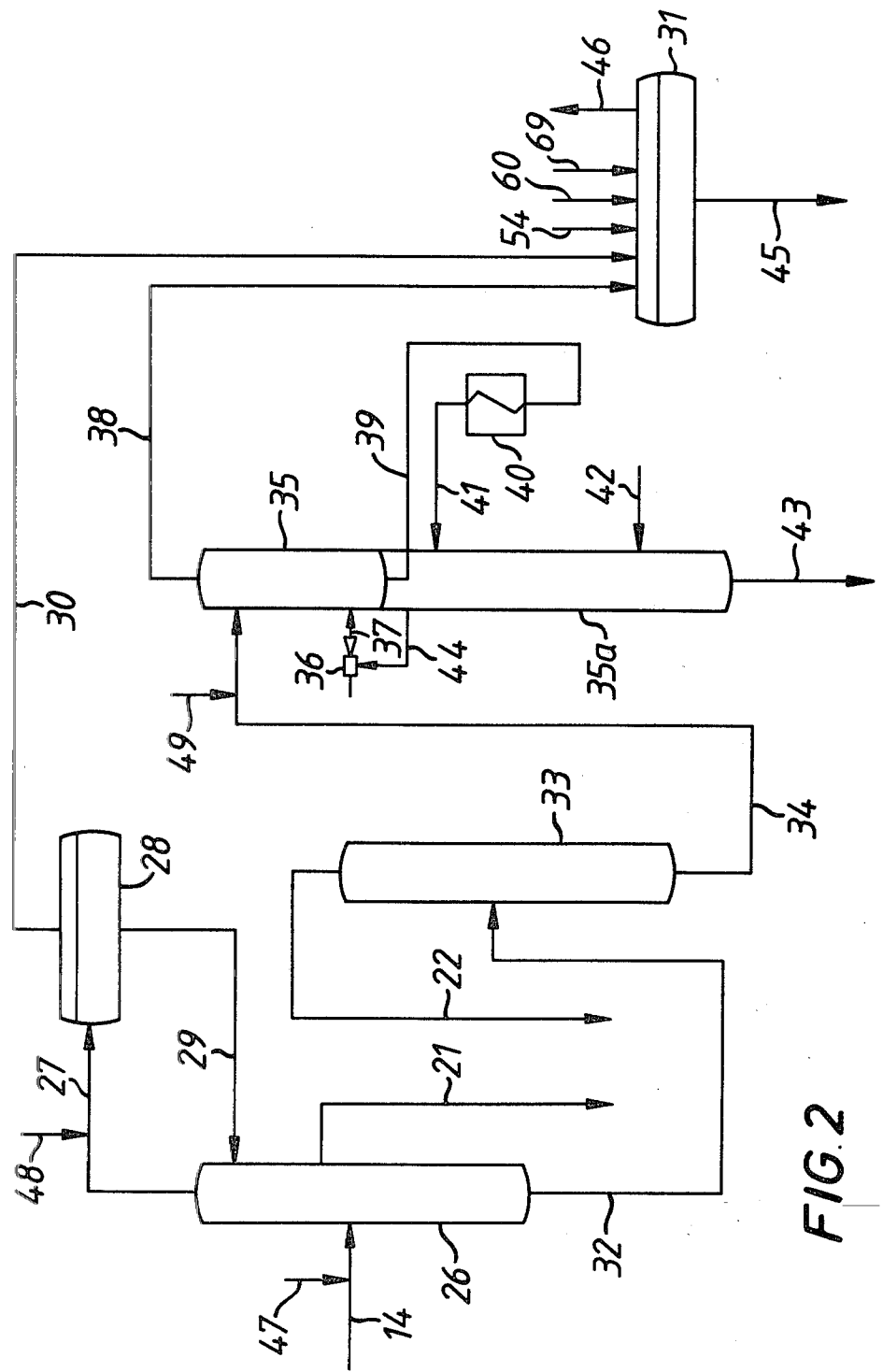
Figure 3:
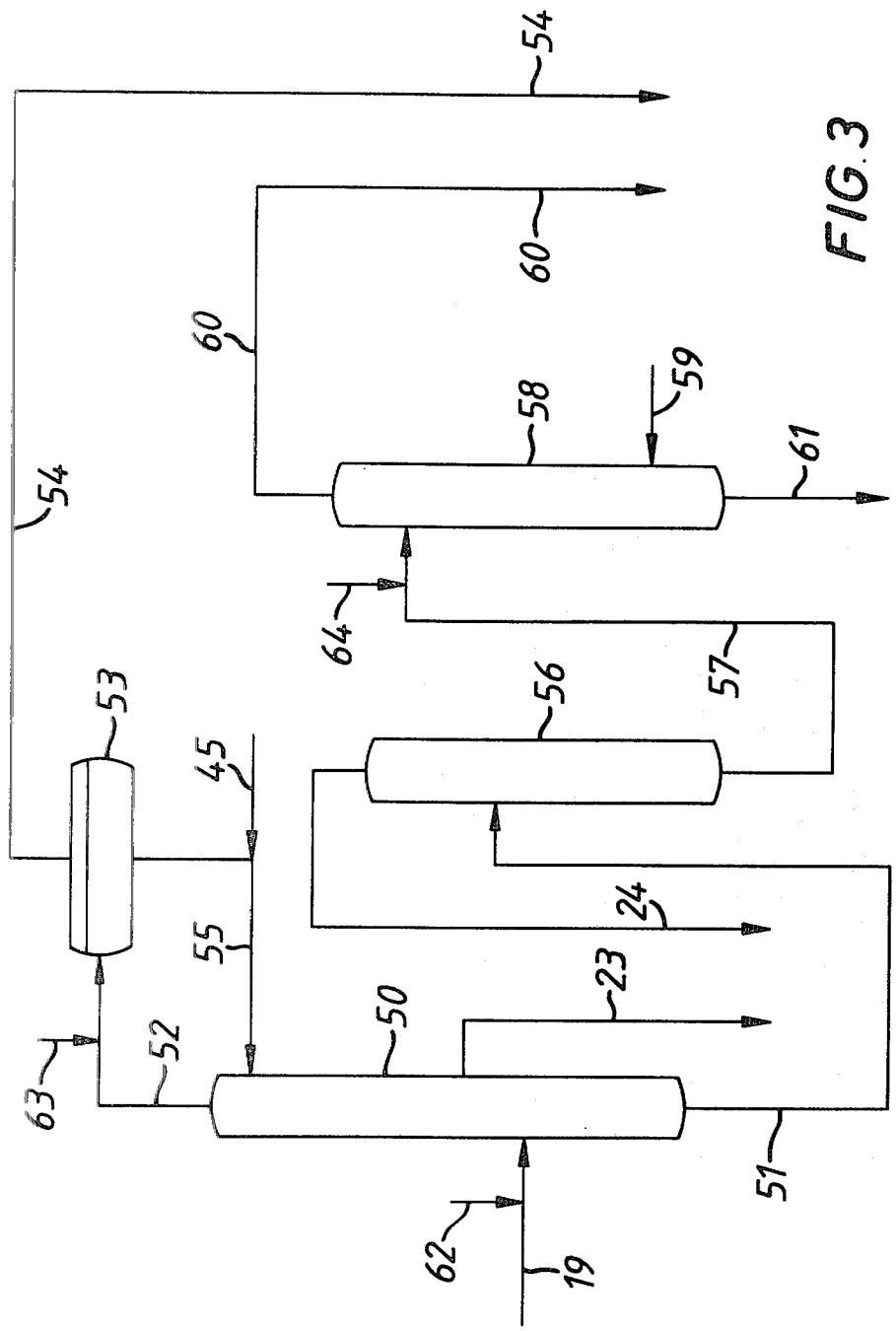
Figure 4:
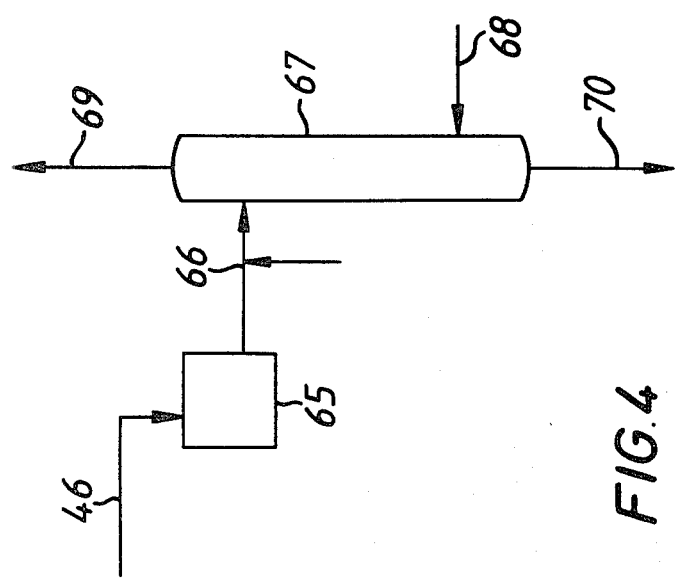

The invention is illustrated with reference to FIGS. 1 to 4 of the accompanying drawings wherein FIG. 1 is a diagram of a conventional solvent dewaxing process, FIG. 2 is a diagram of the solvent recovery system from the dewaxed oil, FIG. 3 is a diagram of the solvent recovery system from the wax and FIG. 4 is a diagram of the neutralisation and distillation system according to the present invention.

FIGS. 1–4 are composite drawings;

FIGS. 1–3 illustrating the prior art but as modified by FIG. 4 they also include essential features of the invention.

One process for the dewaxing of hydrocarbon oils by cooling in the presence of chlorinated solvents and removing the wax which precipitates takes place according to the diagram reproduced in FIG. 1. In this, the waxy oil feedstock fed to the plant through a pipe 1 is diluted with a mixture of dichlorethane and dichlormethane via pipes 2 and 3. In addition the washed filtrate flowing from a vacuum drum cell filter 4 via a pipe 5 passing through an intermediate tank 6 is added to the charge oil for dilution via a pipe 7 after a suitable heat exchange which is not represented in detail.

The oil diluted in this way is cooled in the scraper condensers 8 and 9 by heat-exchange with already dewaxed oil, which is brought forward via a pipe 10, an intermediate tank 11 and a pipe 12, or by evaporating coolant, which is removed via a pipe 13 from a supply system, not shown, to the temperature necessary for the desired degree of dewaxing. The undesired wax contained in the oil separates and is removed continuously by the vacuum drum cell filter 4.

The oil/solvent filtrate after heat exchange with the feedstock in the scraper condenser 8 is fed via a pipe 14 to a multi-stage solvent recovery plant 15, shown in detail in FIG. 2.

The filter cake on the drum cell filter 4 is intensively washed within a given segment by solvent brought via a pipe 16. This solvent has been previously reduced to the requisite low temperature in a heat exchanger 17 with refrigerant from a pipe 18. The wax recovered in this way is fed via a pipe 19 to a multi-stage solvent recovery plant 20, shown in detail in FIG. 3.

The solvent recovered in the two solvent recovery plants 15 and 20 and freed from troublesome water fractions passes via pipe systems 21 and 22 or 23 and 24 back to a supply system 25.

The recovery of the solvent from the oil/solvent filtrate is described in FIG. 2. The oil/solvent mixture enters via the pipe 14 into a column 26, from which a dry solvent stream is withdrawn via pipe 21. This stream returned to the supply system 25 mentioned above. At the top of column 26 a solvent/water mixture is withdrawn via a pipe 27 and passed into a tank 28 where phase separation takes place. The heavier phase consisting of solvent containing water returns via a pipe 29 to the head of the column 26. The lighter phase consisting of water containing solvent travels via a pipe 30 into a tank 31. In the sump of the column 26 an oil still containing solvent is withdrawn via a pipe 32 and passed to a column 33, at the head of which dry solvent is removed via the pipe 22. This solvent stream likewise returns to the supply system 25. Via a bottom pipe 34 oil still containing a slight amount of solvent leaves the column 33. This stream is introduced into a top part 35 of a two-part column. In this separating stage the oil is freed, in counter-current flow with steam which enters near the bottom from a steam ejector 36 via a pipe 37, from further quantities of solvent, which escape together with the steam overhead via a pipe 38. The stream emerging at the bottom of the column section 35 via a pipe 39, after intermediate heating in the heat exchanger 40, is introduced via pipe 41 into the column section 35a and there is freed under vacuum in counter-current flow with steam entering via a pipe 42 from residual traces of the solvent. The solvent-free dewaxed oil is withdrawn via a pipe 43. The steam/solvent mixture passes via a vacuum pipe 44 into the steam ejector 36 and enters together with steam into the column section 35 via the pipe 37. The mixture conducted away through the pipe 38 is fed to the tank 31, where phase separation commences. The lower phase consisting of solvents is fed via a pipe 45 to the solvent recovery system illustrated in FIG. 3 for the wax stream coming from the dewaxing stage. From this recovery plant two streams lead via pipes 54 and 60 into the tank 31; they also consist of a mixture of water and solvent. The water phase still containing a slight amount of solvent in the tank 31 leaves this tank via a pipe 46 and is processed in a special part of the plant illustrated in FIG. 4. From this part of the plant a stream consisting of water and solvent leads out via a pipe 69 into the tank 31. Small quantities of gaseous ammonia are constantly introduced via pipes 47, 48 and 49.

The wax stream containing solvent collected in the dewaxing stage (see FIG. 1) is fed via the pipe 19 to a column 50 (see FIG. 3). Anhydrous solvent leaves the separation stage via the pipe 23 and returns to the supply system 25. At the bottom of the column 50 a wax stream with a reduced content of solvent is withdrawn via pipe 51. Over the head of column 50 a mixture of solvent and water passes via a pipe 52 into a tank 53, where phase separation commences. The aqueous phase passes via the pipe 54 into the separation tank 31 shown in FIG. 2. The heavy phase consisting of solvent containing water from the tank 53 returns via a pipe 55 to the head of the column 50. The pipe 45 bringing the solvent phase from the separation tank 31 shown in FIG. 2 leads into the pipe 55.

The wax stream withdrawn via pipe 51 is passed into a column 56, in which anhydrous solvent is withdrawn overhead via a pipe 24. This returns to the supply system 25. At the bottom of the column 56 a wax stream with a further-reduced content of solvent is withdrawn and introduced via a pipe 57 into a column 58. Here the last residues of solvent are driven off from the wax in counter-current flow with steam which is introduced through a pipe 59. A water/solvent mixture leaves overhead and passes through the pipe 60 into the tank 31. At the bottom of the column 58 solvent free wax is withdrawn via a pipe 61. Small quantities of gaseous ammonia are continuously injected via pipes 62, 63 and 64.

The water phase still containing solvent originating from the tank 31 (FIG. 2) is introduced via the pipe 46 after passing through an intermediate tank 65 (see FIG. 4) via a pipe 66 into an evaporator 67. By distillation with steam, which enters via a pipe 68, a water/solvent mixture is driven off via a pipe 69 which leads into the collector tank 31. At the bottom of the evaporator 67 solvent-free water is withdrawn through a pipe 70.

Together with the water/solvent mixture, which leaves the evaporator 67 overhead, a large part of the hydrochloric acid which is contained in the feedstock for this separation stage, is expelled and passes via the solvent recovery installations into all the process streams. Finally, it is also to be found in the solvent for diluting the feedstock to the dewaxing plant. However, a constant increase in the concentration of hydrochloric acid in the plant as a whole does not occur. Instead, a stationary condition is established, in which part of the hydrochloric acid formed in the process continually leaves the plant at the bottom of the evaporator 67 together with water. The recirculated quantities of hydrochloric acid, however, in conjection with water which is also present, are sufficient to cause serious disorders in many parts of the plant in the course of time.

The addition of ammonia already mentioned at varied points of the two solvent recovery plants does not help substantially to prevent corrosion. As a result of hydrolysis of ammonium chloride in the evaporator 67 hydrochloric acid also gets back into the circuit again. Iron, which is to be found in various process streams in dissolved form as a result of the corrosion, is precipitated by the addition of ammonia. The deposits of iron hydroxides and iron oxides which form at many points in the plants finally lead to stoppages. Traces of iron salts which remain in the oil or wax recovered, affect certain properties of these products in a negative manner. For example, the resistance to ageing is reduced and the tendency to form emulsions is increased.

The difficulties listed are now avoided by the present invention which is operated in the absence of ammonia. The process water containing solvent residues prior to their recovery in the evaporator 67 is neutralised with alkali hydroxides and/or alkali carbonates and/or alkali hydrogen carbonates or is subjected to a neutralising treatment by means of conventional ion exchangers. Preferably this treatment takes place immediately before the evaporator 67, because all the process water streams from which residual quantities of solvent are to be removed are combined in the charge product of this. The neutralisation of the individual process water streams prior to their combination in the tank 31 can also be carried out with advantage.

Further advantages and features of the process of the invention will be seen from the following examples.

EXAMPLE 1a

In the plant described above a mixed-base solvent raffinate with a viscosity of about 115 cSt/50° C. was dewaxed in a quantity of about 30.5 t/hr. In doing so about 24.2 t/hr of dewaxed oil and about 5.8 t/hr of wax were recovered. Despite the continual addition of ammonia to the points indicated and amounting in all to about 0.2 kg/hr, after a short period corrosion occurred throughout the whole plant, especially in the overhead pipes of the solvent recovery installations. Heavy deposits of rust formed in the condensers and the piping and separation systems. The iron content of the water leaving the solvent recovery plants after the evaporator 67 amounted to about 10 ppm.

The demulsification number of the dewaxed oil according to the Institute of Petroleum Standard 19/76 was 250; for the increase in the Conradson coking residue after ageing with the passing through of air pursuant to DIN 51 352; part 1, a value of 1.2 percent by weight was determined.

EXAMPLE 1b

When neutralising the stream of water containing solvent fed to the evaporator 67 with an approximately 10% aqueous caustic soda solution and the simultaneous dispensing with the addition of ammonia to the parts of the installation described above, in the course of one year, only slight corrosion was observed. Practically no rust deposits occurred in the condensers, pipes and tanks. The iron content of the water leaving the plant fell by two powers of ten to 0.1 ppm.

The demulsification number according to IP Standard 19/76 fell to 140; the index for the ageing behaviour pursuant to DIN 51 352, part 1, dropped by 25% to 0.9 percent by weight.

EXAMPLE 2a

In the dewaxing of a mixed-base solvent raffinate with a viscosity of about 32 cSt/50° C., the demulsification number pursuant to IP Standard 19/76 reached a figure of 90; the increase in the Conradson coking residue after ageing by passing through air pursuant to DIN 51 352, part 1, was determined as 0.7%.

EXAMPLE 2b

In the mode of procedure according to the invention in which neutralisation was carried out with 10% aqueous caustic soda solution, the IP Standard 19/76 value was 30, the figure according to DIN 51 352 was 0.5%.

Although in the Examples only the dewaxing of hydrocarbon oils is described, the process of the invention can be applied equally advantageously to plants which are combined directly with a plant for de-oiling of waxes. Such combined plants are known (Hydrocarbon Processing, September 1978, page 181).

The process of the invention is not restricted to the particular embodiment described above. The halogenated hydrocarbons may be recovered from solvent dewaxing, de-oiling and other processes in which they may be employed.

I claim:

1. A process for the dewaxing of an oil fraction which process comprises the steps of contacting the mixture with a halogenated hydrocarbon to obtain one fraction relatively free from halogenated hydrocarbon and one fraction associated with halogenated hydrocarbon and recovering halogenated hydrocarbon from the fraction associated therewith by a recovery system involving the use of steam whereby a contaminated stream of process water containing halogenated hydrocarbon and hydrogen halide is formed, neutralizing said process water stream by treatment with an alkali metal hydroxide, carbonate or hydrogen carbonate, or an ion exchanger, distilling the treated stream to obtain a first fraction containing halogenated hydrocarbon and water, allowing the first fraction to settle into layers of halogenated hydrocarbon and water and recycling the layer of halogenated hydrocarbon to the contacting stage upstream of the neutralization of the process water stream.

2. A process according to claim 1 wherein the contaminated stream of process water is obtained from a process for the solvent dewaxing of a hydrocarbon fraction which comprises the steps of cooling the fraction in the presence of a halogenated hydrocarbon solvent; removing solidified wax; and recovering solvent from the dewaxed fraction and the wax by recovery systems involving the use of steam wherein streams of process water containing halogenated hydrocarbon and hydrogen halide are formed.

3. A process according to claim 1 or 2 wherein the halogenated hydrocarbon is a chlorinated hydrocarbon.

4. A process according to claim 1 or 2 wherein the contaminated stream of process water is neutralized by treatment with sodium hydroxide.

5. A process according to claim 1 or 2 wherein the contaminated stream of process water is neutralized by treatment with 10% wt aqueous sodium hydroxide solution.

6. A process according to claim 1 or 2 wherein the treated stream is distilled in the presence of steam to obtain the first fraction containing halogenated hydrocarbon and water and the second fraction containing uncontaminated water.

* * * * *